United States Patent [19]

Grimm et al.

[11] Patent Number: 4,582,571

[45] Date of Patent: Apr. 15, 1986

[54] SEPARATION OF TANTALUM OR ANTIMONY PENTAFLUORIDE FROM ISOBUTYRYL FLUORIDE AND ANHYDROUS HYDROGEN FLUORIDE

[75] Inventors: Robert A. Grimm; Dace Grote, both of Columbus, Ohio

[73] Assignee: Ashland Oil, Inc., Ashland, Ky.

[21] Appl. No.: 632,747

[22] Filed: Jul. 20, 1984

[51] Int. Cl.$^4$ .............................................. B01D 3/10
[52] U.S. Cl. .................................... 203/91; 202/205; 423/462; 423/488
[58] Field of Search ......................... 203/91; 423/462; 202/205; 423/483, 484, 488, 489; 208/10; 585/710, 375, 724, 747, 464; 260/544 A; 502/36; 562/606

[56] References Cited

U.S. PATENT DOCUMENTS

| | | | |
|---|---|---|---|
| 3,830,871 | 8/1974 | Mayer et al. | 585/747 |
| 3,839,489 | 10/1974 | Mahan et al. | 585/747 |
| 4,064,189 | 12/1977 | Siskin et al. | 585/708 |
| 4,065,381 | 12/1977 | Say et al. | 585/724 |
| 4,065,405 | 12/1977 | Hulme | 502/36 |
| 4,069,268 | 1/1978 | Siskin et al. | 502/36 |
| 4,098,833 | 7/1978 | Wristers | 585/375 |
| 4,105,704 | 8/1978 | Say et al. | 585/464 |
| 4,120,912 | 10/1978 | Hulme | 585/747 |
| 4,144,282 | 3/1979 | McCaulay | 585/747 |
| 4,303,594 | 12/1981 | Norton et al. | 260/544 A |
| 4,451,670 | 5/1984 | Grote et al. | 260/544 A |
| 4,469,804 | 9/1984 | Johnson | 502/36 |

OTHER PUBLICATIONS

Northiko et al., "Reaction of Carbocation Derived from Alkane and Alkyl Methyl Ketones with Carbon Monoxide in Super Acid", Symposium on Advances in Carbocation Chemistry—American Chemical Society, Mar. 20-25, 1983.

*Primary Examiner*—S. Leon Bashore
*Assistant Examiner*—V. Manoharan
*Attorney, Agent, or Firm*—Robert J. Grassi

[57] ABSTRACT

Tantalum ($TaF_5$) or antimony pentafluoride ($SbF_5$) is separated from a product mixture comprised of HF, isobutyryl fluoride and $TaF_5$ or $SbF_5$ by distillation below 760 mm of mercury.

1 Claim, No Drawings

SEPARATION OF TANTALUM OR ANTIMONY PENTAFLUORIDE FROM ISOBUTYRYL FLUORIDE AND ANHYDROUS HYDROGEN FLUORIDE

BACKGROUND OF THE INVENTION a. Field of the Invention

The process is related to the separation of tantalum or antimony pentafluoride from isobutyryl fluoride (IBF) and hydrogen fluoride without substantial decomposition of the pentafluoride and isobutyryl fluoride.

b. Description of the Prior Art

Tantalum or antimony pentafluoride, if used as a catalyst, when separated from the reaction products by hydrolysis, reacts with water and is destroyed (Cotton and Wilkinson, 4th Edition, *Adv. Inorg Chem.* page 834, 835). Hence, their use as catalysts is unsuitable for commercial processes. U.S. Pat. No. 3,830,871 uses liquid/liquid extraction to remove hydrocarbons from HF and $TaF_5$ as a means of separating the pentafluoride without destroying it.

The invention described herein separates the tantalum and antimony pentafluoride by a simple method from a product mixture of a catalyzed reaction so that pentafluoride can readily be recycled and used again, and the isobutyryl fluoride is substantially recovered.

SUMMARY OF THE INVENTION

In a process to form isobutyryl fluoride by the reaction of carbon monoxide, propane, anhydrous hydrogen fluoride and tantalum or antimony pentafluoride, the tantalum or antimony pentafluoride is removed from the anhydrous hydrogen fluoride and isobutyryl fluoride by distilling off the isobutyryl fluoride and anhydrous hydrogen fluoride under vacuum to leave a residue substantially comprised of tantalum or antimony pentafluoride.

DESCRIPTION OF THE INVENTION

The invention is based on the discovery that tantalum or antimony pentafluoride in a mixture of anhydrous hydrogen fluoride and isobutyryl fluoride can be separated under certain distillation conditions described herein in contrast to hydrolyzing the mixture with water to form isobutyric acid and then separating the mixture, or extracting the mixture. Under the distillation conditions discovered, the product is not destroyed by the discovered distillation conditions.

The product mixture of tantalum or antimony pentafluoride, isobutyryl fluoride and anhydrous hydrogen fluoride occurs during the formation of isobutyryl fluoride by the reaction of carbon monoxide, propane and anhydrous hydrogen fluoride and tantalum or antimony pentafluoride under pressure, such as above 100 bars and temperatures near 100° Centigrade. The common practice to remove pentafluoride when used as catalysts has been to hydrolyze such a product mixture. However, the pentafluoride such as antimony or tantalum pentafluoride forms other products, rendering them unsuitable for recycling as a catalyst. Now, however, based on the process described herein, the tantalum or antimony pentafluoride can be recycled for further reaction.

The following Examples illustrate the methods of separation as described herein.

EXAMPLE I

A teflon distillation apparatus without a fractionating column is charged with 10.1 grams of tantalum pentafluoride (37 millimoles (mmole), 30.1 grams of anhydrous hydrogen fluoride (1503 mmole), and 35.9 grams of isobutyryl fluoride (398 mmole). The pot is heated and maintained at a temperature of 33°–36° C., while a vacuum is applied at a pressure of 14 millimeters (mm) Hg using a water aspirator. At the end of a two hour period, the residue in the pot is analyzed and shows 10.1 grams (37 mmole) of tantalum pentafluoride ($TaF_5$), 0.1 grams (5 mmole) of anhydrous hydrogen fluoride, and 2.2 grams (24 mmole) of isobutyryl fluoride (6%). This residue is suitable for recycling.

The distillate contains 30.3 grams (337 mmole) of isobutyryl fluoride (85%), and 31.2 grams (1559 mmole) of anhydrous hydrogen fluoride. The total amount of isobutyryl fluoride recovered from the process is 91%.

EXAMPLE 2

The procedure in Example 1 is followed except that 30 grams of anhydrous hydrogen fluoride, 36 grams of isobutyryl fluoride and 15 grams of tantalum pentafluoride is used. Distillation is performed at atmospheric pressure (760 mm of Hg) over an increasing temperature of from 0° C. to 160° C. for a period of about 2.5 hours; 0.5 hour of which is at 136°–160° C. The recovery of isobutyryl fluoride is about sixty-three percent (63%), and the distillation residue is black and contains some high-boiling material and tantalum pentafluoride. The distillation residue is suitable for recycling.

EXAMPLE 3

Comparative Example

To a 300 cc Autoclave Engineers Magnedrive II Hastelloy C Reactor, 23.5 grams (0.26 moles) isobutyryl fluoride, 23.8 grams (0.09 moles) tantalum pentafluoride ($TaF_5$) and 60 grams anhydrous HF (3.0 moles) are charged, pressurized with CO and held at 20° C. to 109° C. for 2.25 hours (1.1 hours at 109° C.) at a pressure rage of 350–2026 psig (24.1–139.7 bars). After such time the reactor contents are cooled, hydrolyzed with 38 grams (2.1 moles) $H_2O$, vented and emptied by suction over wet ice. Extraction by toluene and cyclohexane from 10% $HF/H_2O$ solution of the reactor contents, yielded 100 milliequivalents (0.1 mole) of carboxylic acids or 38% recovery of isobutyryl fluoride as isobutyric acid. Solvent removal revealed the non-volatiles to be a complex mixture with the major component being isobutyric acid. The average molecular weight of said solvent-free non-volatiles was 190 grams per acid equivalent.

This example shows that even in the presence of CO, when the proper conditions are not used, the isobutyryl fluoride decomposes, in the presence of the very strong acids of the metal pentafluorides in hydrogen fluoride. Thus, necessitating the discovered conditions of distillation to properly recover the isobutyryl fluoride formed, and the metal pentafluoride and hydrogen fluoride for recycling.

Antimony pentafluoride ($SbF_5$) performs similarly and is readily separated from isobutyryl fluoride and anhydrous hydrogen fluoride by distillation, at a pressure from 0.1 to 760 millimeters and a temperature from 0° C. to 140° C., said temperature and pressure conditions are such that the $SbF_5$ does not distill, and the isobutyryl fluoride does not substantially decompose during distillation.

While the invention has been described herein with reference to specific details of certain illustrative embodiments, it is not intended that it shall be limited thereby except insofar as such details appear in the accompanying claims.

We claim:

1. A process for separation of a pentafluoride from a product mixture comprised of anhydrous hydrogen fluoride, isobutyryl fluoride and a pentafluoride selected from the group consisting of antimony pentafluoride ($SbF_5$) and tantalum pentafluoride ($TaF_5$) formed during the reaction of propane, carbon monoxide, anhydrous hydrogen fluoride and the pentafluoride, which comprises:

distilling off the isobutyryl fluoride and anhydrous hydrogen fluoride at a pressure below and up to about one atmosphere, and at a temperature whereby the isobutyryl fluoride does not substantially decompose and the pentafluoride does not substantially distill.

* * * * *